(12) United States Patent
Strobel et al.

(10) Patent No.: US 6,211,185 B1
(45) Date of Patent: Apr. 3, 2001

(54) CONCENTRATE COMPRISING A SULFONAMIDE IN SOLUTION, A 2,4-DIAMINOPYRIMIDINE IN STABLE SUSPENSION WITHIN SAID SOLUTION, AND A SUSPENDING AGENT

(75) Inventors: Michael A. Strobel, Northfield; William A. Soderlund, Jr., St. Peter, both of MN (US)

(73) Assignee: Veterinary Pharmacy Corporation, Northfield, MN (US)

( * ) Notice: Subject to any disclaimer, the term of this patent is extended or adjusted under 35 U.S.C. 154(b) by 0 days.

(21) Appl. No.: 09/304,954

(22) Filed: May 5, 1999

(51) Int. Cl.$^7$ .................... A61K 31/505; A61K 31/18
(52) U.S. Cl. ................... 514/256; 514/260; 514/601
(58) Field of Search .................... 514/256, 250, 514/601

(56) References Cited

U.S. PATENT DOCUMENTS

| | | | |
|---|---|---|---|
| 2,909,522 | 10/1959 | Hitchings et al. | 260/256.4 |
| 3,985,876 | 10/1976 | Hazlett et al. | 424/229 |
| 4,031,214 | 6/1977 | Easterbrook | 424/229 |
| 4,089,949 | 5/1978 | Rumpf | 424/229 |
| 4,332,796 | 6/1982 | Los | 424/229 |
| 5,958,910 | * 9/1999 | Cesura et al. | 514/158 |

OTHER PUBLICATIONS

Sulfakombin et al., Development of the veterinary preparation 1977 (see enclosed abstract).*

Merck Vertiernary Manual, 6th Edition, 1986, pp. 1540–1544.

* cited by examiner

*Primary Examiner*—Kevin E. Weddington
(74) *Attorney, Agent, or Firm*—Wilmer, Cutler & Pickering

(57) ABSTRACT

A palatable antimicrobial drug concentrate comprising: (a) a sulfonamide and/or sulfonamide salt in aqueous solution; (b) a 2,4-diaminopyrimidine in stable suspension within said solution; and (c) a suspending agent. The invention has a long room temperature shelf life and is sufficiently stable to be administered via the drinking water of animals.

20 Claims, No Drawings

CONCENTRATE COMPRISING A SULFONAMIDE IN SOLUTION, A 2,4-DIAMINOPYRIMIDINE IN STABLE SUSPENSION WITHIN SAID SOLUTION, AND A SUSPENDING AGENT

FIELD OF THE INVENTION

The instant invention relates to an antimicrobial concentrate that comprises a sulfonamide and/or sulfonamide salt in combination with a diaminopyrirnidine. More specifically, the instant invention relates to a palatable antimicrobial concentrate, that may be orally administered to animals via their drinking water, that comprises the following components: (a) a sulfonamide and/or salt thereof in solution; (b) a diaminopyrimidine in stable suspension within said solution; and (c) a suspending agent.

BACKGROUND ART

The use of sulfonamides (sulfa drugs) for treating bacterial infections is known. The Merk Veterinary Manual, sixth edition, 1986, pages 1540 through 1544, provides general background on these drugs. It is believed that sulfonamides are effective antibacterial agents because they competitively inhibit an enzymatic step (dihydropterate synthetase) wherein as para-aminobenzoic acid is incorporated into the synthesis of dihydrofolic acid (folic acid). Because folic acid synthesis is reduced, the level of tetrahydrofolic acid (folinic acid) formed from folic acid is also reduced. Folinic acid is an essential component of various coenzymes responsible for single carbon metabolism in cells. Thus, sulfonamides create a domino effect in the body that ultimately results in the suppression of protein synthesis, the impairment of metabolic processes, and an inhibition in the growth and multiplication of organisms that cannot utilize preformed folic acid. The effect is bacteriostatic and, in high concentrations, bactericidal.

2,4-Diaminopyrimidines, such as trimethoprim, are also known antimicrobial agents that have found utility in the treatment of various bacterial and protozoal infections. U.S. Pat. Nos. 2,909,522 and 3,021,332 are two references directed to the formation and use of 2,4-diaminopyrimidines. It is believed that these compounds act by inhibiting an enzyme that facilitates the conversion of folic acid to folinic acid and, thereby, interfering with the biosynthesis of nucleic acids and proteins in bacteria. Typically, 2,4-diaminopyrimidines have a high selectivity for inhibiting the folate synthesis in protozoal enzymes as opposed to folate coenzyme synthesis in host cells. Thus, 2,4diaminopyrimidines are widely used in veterinary antimicrobial compositions.

When sulfonamides are combined with 2,4-diaminopyrimidines, a synergistic antimicrobial effect is often obtained. Although the enhancement in antimicrobial activity is mutual, the 2,4-diaminopyrimidines are often referred to as sulphonamide potentiators. This synergistic antimicrobial activity is very effective against gram-positive and gram-negative bacterial pathogens. The Merk Veterinary Manual, sixth edition, 1986, pages 1544 through 1546, provides general background information on this drug combination.

It would be desirable to combine sulfonamides with 2,4-diaminopyrimidines in a stable palatable concentrate that could be effectively administered to animals via their drinking water, e.g., through the automatic water and Tank water systems utilized in livestock facilities. This type of administration is the most cost effective means of treating large animal populations. Other techniques, such as injection, directly administering tablets or fluids, and powder/food mixtures, have numerous drawbacks. Injection is time consuming, costly, and potentially hazardous because the needle can break off in the animal and/or create an infective injection site. Force feeding tablets and fluids directly to an animal is, minimally, a taxing chore. Mixing sulfonamide and 2,4-diaminopyrimidine powders into an animal's food creates a bad tasting mixture that the animal is less likely to ingest, making it difficult to insure that even dosages are administered.

Unfortunately, 2,4-diaminopyrimidines and many sulfonamides exhibit poor solubility in water. Although techniques exist to increase the solubility of each compound individually, these techniques are incompatible. Sulfonamides are solubilized in water by the addition of a pharmaceutically acceptable inorganic base whereas 2,4-diaminopyrimidines are solubilized in water by the addition of a pharmaceutically acceptable acid. If the acidic and basic solutions are mixed, the sulfonamide and 2,4-diaminopyrimidine components precipitate out of solution.

Furthermore, in aqueous compositions where the pH approaches 7.0, sulfonamides and 2,4-diaminopyrimidines combine, in a 1 to 1 molar ratio, to form an insoluble and undesirable complex. Given that city water generally has a pH between 7.0 and 7.5, the formation of this complex is hard to avoid when the two compounds are placed into automatic or Tank water systems.

Attempts have been made to generate aqueous solutions containing both sulfonamides and 2,4-diaminopyrimidines by adding various types of water-miscible organic solvents, such as dimethylacetamide and low molecular weight polyalkylene glycols. U.S. Pat. Nos. 3,985,876, 4,031,214, and 4,089,949 are representative of this art. These solutions, which are primarily utilized in injection procedures, are not suitable for use in automatic water and Tank water facilities. The organic solvent's ability to promote solubility is quickly diminished by large scale dilution in water. Furthermore, large scale dilution in water typically brings the pH near 7.0, which is often outside the pH parameters necessary to maintain the solutions.

Compositions containing sulfonamides in solution and 2,4-diaminopyrimidine potentiators in suspension have also been made. U.S. Pat. Nos. 4,031,214 and 4,332,796 are representative of this art.

U.S. Pat. No. 4,031,214 describes an injectable preparation that comprises a suspension of finely divided potentiator within an aqueous solution containing a pharmaceutically acceptable water soluble salt of a sulphonamide and a strong base. The term potentiator is defined in the patent to include many types of 2,4-diaminopyrimidines. The pH of the preparation is stated to be at least 10 to avoid the growth of crystalline complexes. U.S. Pat. No. 4,031,214 does not disclose that the composition can be orally administered either directly or through drinking water. Furthermore, the patent does not disclose a suspending agent. Finally, it is clear from the pH parameters required in the patent that the composition described therein would not be useful in livestock drinking water where the pH typically approaches 7.0.

U.S. Pat. No. 4,332,796 describes potentiated sulfonamide compositions useful for intramuscular injection. The compositions comprise mixtures of alkali metal sulfonamides with microcrystalline potentiators wherein the microcrystals have been coated with mixtures of phospholipids and non-ionic surfactants. The compositions are alleged to be advantageous because they can be used for injection with the addition of sterile water. Furthermore, it is alleged that the resulting aqueous preparations are stable for long periods of time. The potentiator component preferably belongs to the 2,4-diaminopyrimidine class of compounds. The injectable mixture, with sterile water, has a pH in the advantageous range of 8.5–9.5. U.S. Pat. No. 4,332,796 does not disclose that the composition can be orally administered either directly or through drinking water. Furthermore, the patent does not disclose the use of a suspending agent. In fact, the reference teaches that suspending agents are undesirable because they provoke irritation at the injection site, lower chemotherapeutic diffusion in tissues and a decrease in injectability. Finally, it is clear from the high pH parameters required by the patent that the composition described therein would not be useful in livestock drinking water where the pH typically approaches 7.0.

Thus, there remains a need in the art for an antimicrobial concentrate that comprises a sulfonamide and/or salt thereof in combination with a diaminopyrimidine that may be orally administered to animals via their drinking water. To be economically feasible, the concentrate would have a room temperature shelf life of at least several days. In addition, when the concentrate is diluted in sufficient water to bring the pH near 7.0, the components in the concentrate would have to remain dissolved and/or suspended for at least a day.

SUMMARY OF THE INVENTION

The invention is a palatable antimicrobial drug concentrate that can be orally administered to an animal in combination with its drinking water, comprising: (a) a sulfonamide and/or sulfonamide salt in aqueous solution; (b) a 2,4-diaminopyrimidine in stable suspension within said solution; and (c) a suspending agent. The aqueous solution is preferably organic solvent free. Component (a) is most preferably sodium sulfadiazine. Component (b) is most preferably micronized or ultramicronized trimethoprim. Component (c) is most preferably xanthan gum. The palatibility of the 2,4-diaminopyrimidine in the concentration is improved by coating, sweetening and flavoring the suspended 2,4-diaminopyrimidine to reduce its adverse taste. The concentrate exhibits a long term room temperature shelf life which exceeds 10 days and often is best measured in years. In addition, the components of the concentrate, when diluted by water to a pH within the range of 7.0 to 7.5, remain stable for at least 24 hours.

DISCLOSURE OF THE INVENTION

The instant invention relates to a antimicrobial concentrate comprising a suspension of a 2,4-diaminopyrimidine in an aqueous solution containing a sulfonamide and/or sulfonamide salt. From the perspective of taste, it is preferred that the 2,4-diaminopyrimidine be in the form of a suspension since this better masks the bitter taste of the drug.

The concentrate contains three critical components in addition to the water carrier. The first component is a sulfonamide and/or sulfonamide salt in aqueous solution. The second component is a 2,4-diaminopyrimidine suspended within said aqueous solution. The third component is a suspending agent which coats the 2,4-diaminopyrmidine compound and enhances the stability of the suspension. In addition, a number of other optional components are preferably added. These optional components include antioxidants, preservatives, surfactants, sweeteners, and flavoring agents.

The sulfonamide is added as an antimicrobial agent and any sulfonamide known in the art for this purpose may be utilized in the instant invention. Sulfonamides, also known as sulfa drugs, are generally derived from sulfanilic acid and are represented by the following formulae (i) through (iv):

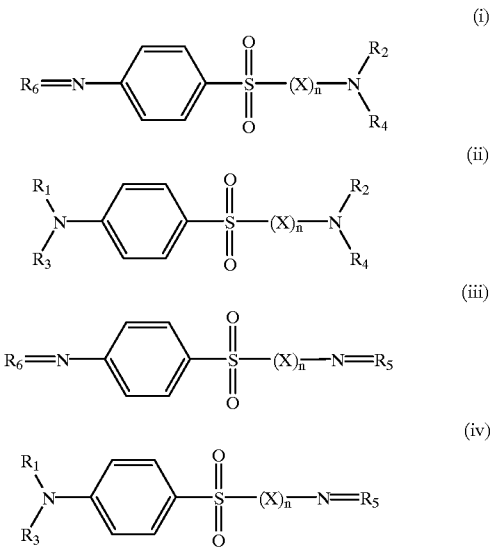

wherein n equals zero or one and X, if present, is a phenyl moiety, and wherein $R_1$ through $R_8$ are, independently, selected from hydrogen and any organic moiety containing up to 20 atoms.

Sulfonamides corresponding to formulae (i) through (iv) include disulfamethoxypyridazine, sulfacetamide, sulfamidochyrsoidine, sulfanilamide, 4-sulfanilamidosalicylic acid, $N^4$-sulfanilylsulfanilamide, sufanilylurea, N-sulfanilyl-3,4-xylamide, 2-p-sulfanilylanilinoethanol, sulfabenz, sulfabenzamide, sulfacytine, sulfachrysoidine, sulfadiazine, sulfadicramide, sulfadimethoxine, sulfadoxine, sulfaethidole, sulfaethoxypyridazine, sulfafurazole, sulfaguanole, sulfisomidine, sulfisoxazole, sulfalene, sulfaloxic acid, sulfamerazine, sulfameter, sulfamethazine, sulfamethoxypyridazine, sulfanitran, sulfapyridazine, sulfamethoxazole, sulfamethylthiazole, sulfametrole, sulfamoxole, sulfamethizole, sulfamethomidine, sulfaoxazole, sulfaperine, sulfaphenazole, sulfaproxyline, sulfapyrazine, sulfapyridine, sulfaquanidine, sulfaquinoxaline, sulfasomizole, sulfasymazine, sulfasalizine, sulfatolamide, sulfathiazole, sulfathiourea, sulfatolamide, sulfazamet, halogen and/or $C_{1-4}$ alkyl substituted variations thereof, and the like.

Preferably, either all of the $R_{1-8}$ groups present on the sulfonamides are hydrogen or all but one of the $R_{1-8}$ are hydrogen. More preferably, the sulfonamides are represented by the following formula (v):

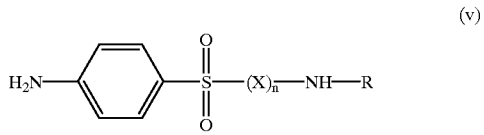

wherein n is one or zero, X is a phenyl moiety, and R is hydrogen or an organic moiety containing up to 20 atoms. These more preferred sulfa drugs exhibit the best balance between effectiveness and cost. The most preferred sulfonamides are sulfadiazine, sulfanilamide, sulfisoxazole, sulfaoxazole, and sulfapyridine, with sulfadiazine being the sulfa drug of choice.

The sulfonamides may be salified to increase their water solubility. In fact, this is a necessary step if water insoluble, or only slightly soluble, sulfonamides are employed. The salts may be prepared by a variety of known techniques. For example, the sulfonamide may be dissolved in an alcoholic medium followed by the addition of an alkali hydroxide alcoholic solution causing the desired salt to precipitate out of solution. Alternatively, it is also possible to combine the process for making the sulfonamide salt with the process for making the inventive concentration by reaction of the sulfonamide with bases in aqueous solution. Substances that can be used to form such salts are, for example, all alkalies (preferably sodium hydroxide), and organic amines (preferably alkanolamines such as ethanolamine, tri (hydroxymethyl)aminomethane and diethanolarnine).

For example, the most preferred sulfonamide for use in this invention is sulfadiazine. Sulfadiazine is only slightly soluble in water. Therefore, sulfadiazine is generally added in the form of an alkali metal salt such as sodium sulfadiazine and optionally in combination with a base such as diethanolamine.

The sulfonamide in this invention is present in an amount of at least 2% and no more than 55%, based on the entire weight of the composition. Preferably, the sulfonamide represents 25% to 50% of the composition. Most preferably, the sulfonamide is 45% to 50% of the composition.

The 2,4-diaminopyrimidine is also added as an antimicrobial agent and, preferably, serves as potentiator for the sulfonamide. Any known 2,4-diaminopyrimidine may be utilized in the invention. Preferred 2,4 diaminopyrimidines include 2,4-diamino-5-benzylpyrimidines having the following formula (vi):

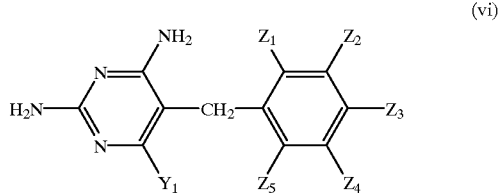

(vi)

wherein $Y_1$ is hydrogen or an alkyl having four or less carbon atoms, and wherein $Z_{1-5}$ are, independently, selected from hydrogen, an alkoxy group having four or less carbon atoms such as methoxy and isobutoxy, an amino group, a nitro group, halogens such as chlorine and bromine, an alkyl or substituted alkyl group having four or less carbon atoms such as methyl and trifluoromethyl, and a hydroxyl group. Suitable preferred potentiators corresponding to the preceding formula include 2,4-diamino-5-(3,4,5-trimethoxybenzyl) pyrimidine (a.k.a. trimethoprim), 2,4-diamino-5-(3,4-dimethoxybenzyl) pyrimidine (a.k.a. diaveridine), 2,4 diamino-5-(3,4,6-trimethoxybenzyl) pyrimidine, 2,4-diamino-5-(2-methyl-4,5-dimethoxybenzyl) pyrimidine (a.k.a. ormetoprim), 2,4-diamino-5-(3,4-dimethoxy-5-bromobenzyl) pyrimidine, and 2,4-diamino-5-(4-chlorophenyl)-6-ethylpyrimidine (a.k.a. pyrimethamine). The most preferred 2,4-diaminopyrimidine it trimethoprim.

The 2,4-diaminopyrimidine is preferably added in particulate micronized or ultramicronized form. By micronized, it is meant that the 2,4-diaminopyrimidine has a particle size (average diameter) within the range of $1\mu$ to $100\mu$. Ultramicronized particles are a subgroup of micronized particles and have a particle size of $0.25\mu$ to $10\mu$. As the trimethoprim particle size gets smaller, it becomes easier to maintain the suspension.

The 2,4-diaminopyrimidine in this invention is present in an amount of at least 0.4% and no more than 18.5%, based on the entire weight of the concentrate. Preferably, the 2,4-diaminopyrimidine represents 5% to 16.5% of the concentrate. Most preferably, the 2,4-diaminopyrimidine is 9.0% to 10% of the concentrate.

The ratio of sulfonamide and/or sulfonamide salt to 2,4-diaminopyrimidine in the concentrate can range from 10:1 to 0.1:1 (w/w). Preferably, however, the ratio of sulfonamide and/or salt thereof to 2,4-diaminopyrimidine is approximately 3:1 to 5:1. The most preferred ratio of sulfonamide and/or salt thereof to 2,4-diaminopyrimidine is approximately 4:1.

The suspending agent is added to coat the suspended particles and, thereby, prevent them from sticking together. When particles stick together they become heavier and more easily fall out of suspension. The suspending agent not only stabilizes the suspension but also permits a higher percentage of suspended particles to be incorporated into the suspension.

Any pharmaceutically acceptable suspending agent may be employed in the invention including water soluble polysaccharide gums and cellulose derivatives such as methyl cellulose, carboxymethylcellulose and hydroxypropylmethylcellulose. However, the water soluble polysaccharide gums have proven to give superior results. Suitable water soluble polysaccharide gums include xanthan gum, guar gum, and gum arabic.

In particular, it has been discovered that xanthan gum generates the highest suspension stability and, thereby, enables higher concentrations of 2,4-diaminopyrimidine to be maintained in suspension. Xanthan gum is a high molecular weight heteropolysaccharide composed of D-glucose, D-mannose, and D-glucuronic acid. Numerous studies indicate that xanthan gum has a molecular weight of approximately 2 million. Xanthan gum dissolves in acidic solutions, is compatible with most basic compounds, and exhibits unusual stability in the presence of most salts.

The suspending agent in this invention is present in an amount of at least 0% and no more than 5%, based on the entire weight of the concentrate. Preferably, the suspending agent represents 0% to 2% of the concentrate. Most preferably, the suspending agent is 0% to 0.35% of the concentrate.

Preferably, surfactants (surface active agents) are also added in order to increase the spreading and wetting properties. In general, surfactant molecules have two dissimilar ends. One end is water soluble (highly polar or hydrophillic) and the other end is water insoluble (non-polar or hydrophobic). At the particle-water interface, the hydrophillic group will associate with the water and the hydrophobic end with the particle. This action reduces surface tension and aids suspension of the particles in the water. Surfactants are classified as anionic, cationic and non-ionic depending on the electric charge of their active groups.

Any pharmaceutically acceptable surfactant known in the prior art may be used in the invention. Preferably the surfactants are nonionic surfactants. Particularly preferred nonionic surfactants are polysorbates. Polysorbates are polyoxethylene fatty acid esters. Polysorbates are obtained by the esterification of sorbitol with a fatty acid such as stearic acid, lauric acid and palmitic acid under conditions that cause splitting out of water from the sorbitol, leaving sorbitan. About 20 moles of ethylene oxide per mole of sorbitol are used in the condensation to effect water solution. Suitable polysorbates include polysorbate 20 (polyoxyethylene (20) sorbitan monolaurate), polysorbate 60 (polyoxyethylene (20) sorbitan monostearate), polysorbate 65 (polyoxyethylene (20) sorbitan tristearate), and polysorbate 80 (polyoxyethylene (20) sorbitan monooleate). A preferred surfactant is polysorbate 80.

When surfactants are employed, they are generally present in an amount of at least 0% and no more than 3%, based on the entire weight of the concentrate. Preferably, the surfactants represent 0% to 2% of the concentrate. Most preferably, the surfactants are 0% to 1.697% of the concentrate.

Preferably, sweeteners are also added to counter the bitter taste of the 2,4-diaminopyrimidine. The sweeteners are selected from any natural and/or synthetic compounds capable of overcoming the bitterness of the drug. Natural sweeteners include carbohydrates such as sucrose, dextrose, fructose, invert sugar, mannitol, sorbitol, and the like. Synthetic sweeteners include saccharin, aspartame, cyclamates, and other so-called artificial sweeteners that are familiar to those of skill in the art.

When a sweeteners are employed, they are generally present in an amount of at least 0% and no more than 65%, based on the entire weight of the concentrate. Preferably, the sweeteners represent 0% to 5% of the concentrate. Most preferably, the sweeteners are 0% to 2% of the concentrate.

Preferably, flavoring agents are also added to give the 2,4-diaminopyrimidine a recognizable and pleasing taste. The flavoring agents may be any natural or synthetic compounds that provide an acceptable taste to the composition. Such flavoring agents include bubble gum, fruit flavorings (such as grape, cherry, berry, and citrus), mint flavorings (such as peppermint and spearmint), vanilla, chocolate, and the like.

When flavoring agents are employed, they are generally present in an amount of at least 0% and no more than 10%, based on the entire weight of the concentrate. Preferably, the flavoring agents represent 0.1% to 5% of the concentrate. Most preferably, the flavoring agents are 0.25% to 0.44% of the concentrate.

Preferably, antioxidants are employed in the invention to prevent oxidation of the antimicrobial agent(s) in the presence of oxygen. Any pharmaceutical grade antioxidants that dissolve into the solution of the invention cant be used. Examples of antioxidants useful in the invention include sodium metabisulfate, ascorbic acid, sodium formaldehyde, sulfoxylate, or mixtures thereof. A preferred antioxidant is sodium metabisulfate.

When antioxidants are employed, they are generally present in an amount of at least 0% and no more than 5%, based on the entire weight of the concentrate. Preferably, the antioxidants represent 0.1% to 0.2% of the concentrate. Most preferably, the antioxidants are 0.12% to 0.1334% of the concentrate.

Preferably, preservatives are used in order to extend the shelf life of the liquid pharmaceutical solutions of the invention by limiting the amount of microorganisms in the solution. Any type of pharmaceutical grade preservatives that are completely soluble in the solution of the invention are useful. Examples of suitable preservatives include butyl paraben, methylparaben, polyparaben, and mixtures thereof.

When preservatives are employed, they are generally present in an amount of at least 0% and no more than 1.0%, based on the entire weight of the concentrate. Preferably, the preservatives represent 0% to 0.01% of the concentrate. Most preferably, the preservatives are 0% to 0.008% of the concentrate.

The principal carrier for the concentrate is water. Preferably, the water is substantially organic solvent free and, more preferably, completely organic solvent free. By "substantially organic solvent free" it is meant that organic solvents make up no more than 5% of the concentrate. Organic solvents are undesirable because they effect the taste of the concentrate and, when mixed, they are not stable in the time range of 8 12 hours.

There is no real limit to the amount of water that can be employed in the concentrate as long as sufficient water is employed to maintain the sulfonamide and/or sulfonamide salt in solution and the 2,4-diaminopyrimidine in suspension. However, since the composition is a concentrate, it is preferred to limit the water as much as possible to reduce the size of the product to aid handling and storage.

Generally, the water carrier is present in an amount of at least 40% and no more than 90%, based on the entire weight of the concentrate. Preferably, the water represents 50% to 80% of the concentrate. Most preferably, the water is 65% to 70% of the concentrate.

The pH of the concentrate will obviously depend on a number of factors, including the water concentration. However, generally, the concentrate has a pH at or above 10.

One of the benefits of the concentrate is that it exhibits a long shelf life at room temperature. By "shelf life" it is meant that the sulfonamide or sulfonamide salt stays in solution, that the 2,4-diaminopyrimidine stays in suspension, and that both of these components maintain their antimicrobial properties. Depending on the components and concentrations, the shelf life of the concentrates made in accordance with the invention ranges from at least 10 days to three years or more at room temperature.

Any animal may be treated with the composition. Suitable animals include humans, domestic animals (such as livestock, e.g., pigs, beef and dairy cattle, horses, poultry, and sheep), pets (such as dogs, cats, and the like), and non-domestic animals such as deer, buffalo, elk, and the like, that are kept in herds and fed from a controlled water supply.

A major benefit of the concentrate is that it can be effectively administered by dilution into the drinking water of large animal populations, e.g. addition into the automatic water and Tank systems in livestock facilities. City water generally has a pH between 6.0 and 8.0. Therefore, it is necessary in such applications that the components in the diluted concentrate remain stable over the entire pH range of 7.0 to 7.5. By "stable", it is meant that for at least 24 hours after the concentrate has been diluted with water, the sulfonamide or sulfonamide salt remains in solution, the 2,4-diaminopyrimidine remains in suspension, and there is no appreciable complex formation. It has been discovered that the compositions of the instant invention remain stable for at least 12, and often 96 hours or more, when diluted with sufficient water to bring the pH within the range of 7.0 to 7.5.

The dosage of concentrate that is administered is guided by the judgment of the health care provider after taking into consideration a number of factors including the type of animal, the size of the animal, the type of infection being treated, and whether the treatment is preemptive or responsive to an existing condition. However, the dosage should always be such that the targeted gram positive or gram negative bacterial infection or infections can be treated. These types of bacteria include: Steptococci; Staphylococci; actinobacillie; actinomyceae; Salmonella; Pasteurella; Pneumococci; Proteus; *E. Coli*; Coynebacteria; Vibrio; Bordetelle; Brucella; Klebsiellae; Haemophilae; and Enterobacter species such as Morganella, Shigella and *Pneumocystis Carinii*.

Preferably, however, the dosage of concentrate to final drinking water is 1 ounce of concentrate per gallon of drinking water. More preferably, the dosage is 300 ml of concentrate per gallon of stock solution the first day of treatment and 150 ml of concentrate per gallon of stock solution on each day thereafter.

The following examples are intended to illustrate, but not limit, the invention:

EXAMPLE 1

Formation of First Inventive Concentration 80 gm sodium metabisulfate, 760 ml diethanolamine, 76 ml polysorbate 80, 3600 ml concentrated sodium saccharin, and 250 ml cherry concentrate were added to 45,000 ml of deionized water. The solution was stirred until all of the components were dissolved. 25 Kg of sodium sulfadiazine was then slowly added, followed by approximately 30 minutes of stirring to insure that the sodium sulfadiazine dissolved into the solution. The solution was then diluted to 60,000 ml with deionized water and filtered twice through a coarse filter. 6800 gm of trimethoprim having a particle size of $14\mu$ was added followed by thorough stirring to suspend the trimethoprim in the solution. 200 gm of xanthan gum was then added and the composition was vigorously stirred until the xanthan gum became fully hydrated and all of the trimethoprim particles were coated. The composition was then diluted to 68200 ml with deionized water and dispensed into containers The final mixture has 400 mg/ml sulfadiazine and 100 mg/ml timethoprim.

EXAMPLE 2

Formation of Second Inventive Concentration

A composition was formulated in the same manner set forth in Example 1 with the exception that the particle size of the trimethoprim is less than 4 microns. Note that although 200 gm xanthan gum was once again utilized, the lower particle size of the trimethoprim would have permitted a substantial lowering in the amount of xanthan gum employed. This formulation enabled a longer duration suspension—up to 96 hours in stock solution and several weeks in the concentrate.

EXAMPLE 3

Formation of Comparative Concentration

A composition was made in accordance with Example 1 with the exception that no xanthan gum was employed.

EXAMPLE 4

The inventive and comparative concentrations created in Examples 1, 2 and 3 were added to six 128 gallon samples of drinking water. The six samples included 150 ml per gallon and 300 ml per gallon samples of the inventive concentration from Example 1, 150 ml and 300 ml per gallon samples of the inventive concentration from Example 2, and 150 ml and 300 ml per gallon samples of the comparative concentration in Example 3. The 150 ml gallon samples are 12.89 mg/kg dosages of the drug and the 300 ml per gallon samples are 25.78 mg/kg dosages of the drug.

A field trial using pigs was then conducted to compare the effectiveness of the concentrations. In the trial, the 12.89 mg/kg dosages were used in the first day and the 25.78 mg/kg dosages were used in days 2 to 7. The results are summarized in the following Table 1:

TABLE 1

| Treatment | Water consumed per day by 1000 30 lb. pigs | Dose as delivered per pig (150 cc per gallon of stock water) | Dose as delivered per pig (300 cc per gallon of stock water) |
|---|---|---|---|
| Example 1 | 395 gallons | 231.44 mg | 462.88 mg |
| Example 2 | 398 gallons | 233.20 mg | 466.40 mg |
| Control (no treatment) | 402 gallons | N/A | N/A |
| Example 3 (no xanthan coating) | 301 gallons | 176.37 mg | 352.74 mg |

The trimethoprim in the comparative Example 3 formulation dropped out of suspension within 20 minutes to one hour. In contrast, the formulations of Examples 1 and 2 remained in suspension for the full day of each administration. As evidenced by Table 1, the net result was the ability to maintain the suspension for a longer duration allowed the pigs to injest more of the antimicrobial formulation in Examples 1 and 2.

EXAMPLE 5

A field trial was conducted comparing the effectiveness of 50 cc of the concentration in Example 1 versus 454 cc of a commercially available sulfamethoxizole/trimethoprim suspension that is utilized in human pediatric medicine (herein referenced as "Smz/Tmp Human"). The comparison related to the treatment of a bacterial respiratory disease in pigs caused by *Haemophilis Parasuis* and *Pasturella Multocida*. Sensitivity was confirmed to both preparations by bacteriology. The results are outlined in the following Table 2:

TABLE 2

| Treatment | Number of Animals in the Group | Number of Sick Animals in the Group | Mortalities after 14 Days of Treatment due to Sickness | Number of Culls at Slaughter |
|---|---|---|---|---|
| Example 1 | 508 | 263 | 3 | 6 |
| Smz/Tmp Human | 502 | 275 | 35 | 28 |
| Control (no treatment) | 506 | 269 | 52 | 32 |

Note that it is impossible to dose more than 3 pints of Smz/Tmp Human suspension per gallon of stock solution and that the trimethoprim in the Smz/Tmp Human suspension falls out of suspension within 5 minutes resulting in severe under dosing of the product as compared to the inventive concentration from Example 1. Thus the Smz/Tmp Human treatment is 11 to 12 time more ineffective in preventing mortality. This was one of the principle motivators behind the development of the invention.

EXAMPLE 6

The efficacy of the inventive embodiment described in Example 2 and Smz/Tmp Human against *E. Coli* K-88 serotype in 25 pound nursery pigs with diarrhea. The process was substantially identical to the process described in the preceding Example 5. Note that Smz/Tmp Human is the product currently being used commercially. The results are set forth in the following Table 3:

TABLE 3

| Treatment | Number of pigs in group | Mortality in pigs after treatment started | Mortality in pigs prior to treatment |
|---|---|---|---|
| Example 2 | 325 | 2 | 185 |
| Smz/Tmp Human | 325 | 24 | 182 |
| Control (no treatment) | 50 | 5 | 25 |

This demonstration demonstrates the superior dosing and consequently the superior efficacy of the inventive formulations compared to tradition sulfonamide/trimethoprim suspension treatments.

While the invention has been described in conjunction with the specific embodiments outlined above, it is evident that many alternatives, modifications, and variations will be apparent to those skilled in the art. In example, some steps may be eliminated or performed out of sequence. Accordingly, the preferred embodiments of the invention are intended to be illustrative and not limiting. Various changes may be made without departing from the spirit and scope of the invention as defined in the claims.

What is claimed is:

1. A palatable antimicrobial drug concentrate, that may be orally administered to an animal in combination with its drinking water, comprising:
   (a) a sulfonamide and/or sulfonamide salt in aqueous solution;
   (b) a 2,4-diaminopyrimidine in stable suspension within said solution; and
   (c) a suspending agent.

2. The concentrate of claim 1, wherein the sulfonamide is selected from the compounds corresponding to the following formula:

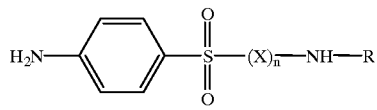

wherein n is one or zero, X, if present, is a phenyl moiety, and R is hydrogen or an organic moiety containing up to 20 atoms, and wherein the sulfonamide salt is selected from alkali metal salts of said formula.

3. The concentrate of claim 1, wherein component (a) is sodium sulfadiazide.

4. The concentrate of claim 1, wherein the 2,4-diaminopyrimidine corresponds to the formula:

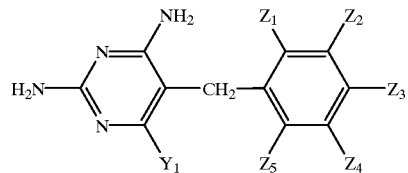

wherein $Y_1$ is hydrogen or an alkyl having four or less carbon atoms, and wherein $Z_{1-5}$ are, independently, selected from the group consisting of hydrogen, an alkoxy group having four or less carbon atoms, an amino group, a nitro group, a halogen, an alkyl or substituted alkyl group having four or less carbon atoms, and a hydroxyl group.

5. The concentrate of claim 1, wherein the 2,4-diaminopyrimidine is selected from the group consisting of trimethoprim, diaveridine, 2,4-diamino-5-(3,4,6-trimethoxybenzyl) pyrimidine, ormetoprim, 2,4-diamino-5-(3,4-dimethoxy-5-bromobenzyl) pyrimidine, and pyrimethamine.

6. The concentrate of claim 1, wherein the 2,4-diaminopyrimidine has a particle size of 1 $\mu$ to 100 $\mu$.

7. The concentrate of claim 1, wherein the sulphonamide and/or sulphonamide salt is present in an amount of 2% to 55% and the 2,4-diaminopyrimidine is present in an amount of 0.4% to 16.5%, based on the entire concentrate, and wherein the ratio of the sulphonamide and/or sulfonamide salt to 2,4-diaminopyrimidine is approximately 3:1 to 5:1.

8. The concentrate of claim 1, wherein the suspending agent is selected from the group consisting of polysaccharide gums and cellulosic derivatives.

9. The concentrate of claim 1 wherein the suspending agent is xanthan gum.

10. The concentrate of claim 1, wherein the suspending agent is present in the amount of 0% to 5%, based on the entire concentrate.

11. The concentrate of claim 1, additionally comprising one or more surfactants.

12. The concentrate of claim 1, additionally comprising a polysorbate surfactant.

13. The concentrate of claim 1, wherein the composition additionally comprises one or more antioxidants, preservatives, sweeteners, and flavoring agents.

14. The concentrate of claim 1 comprising sodium sulfadiazine, trimethoprim, xanthan gum, a surfactant, and one or more compounds selected from the group consisting of antioxidants, preservatives, sweeteners and flavoring agents.

15. The concentrate of claim 1, wherein components (a) and (b) exhibit stability upon dilution with water to a pH of 7.0 to 7.5 such that, for at least 24 hours, the sulfonamide or salt thereof remains in solution, the 2,4-diaminopyrimidine remains in suspension, and insoluble complexes do not form.

16. The concentrate of claim 1, wherein the room temperature shelf life is at least 10 days.

17. A method of orally administering a drug containing a sulfonamide and/or salt thereof and a 2,4-diaminopyrimidine to an animal comprising the following steps:
   a) forming a palatable antimicrobial concentrate that comprises a sulfonamide and/or sulfonamide salt in aqueous solution, a 2,4-diaminopyrimidine in stable suspension within said solution, and a suspending agent;
   b) adding said concentrate to the drinking water of an animal; and
   c) allowing the animal to drink the drinking water.

18. The method of claim 17, wherein the components (a) and (b) in the concentrate exhibit stability upon dilution with water to a pH of 7.0 to 8.0 such that, for at least 24 hours, the sulfonamide or salt thereof remains in solution, the 2,4-diaminopyrimidine remains in suspension, and insoluble complexes do not form.

19. The method of claim 17, wherein the sulphonamnide and/or sulphonamide salt are present in the concentrate in an amount of 2% to 55%, the 2,4-diaminopyrimidine is present in the concentrate in an amount of 0.4% to 18.5%, the ratio of the sulphonamide and/or sulfonamide salt to 2,4-diaminopyrimidine within the concentrate is approximately 3:1 to 5:1, and the concentrate is added to the drinking water in an amount of 1 ounce of concentrate per gallon of drinking water.

20. A palatable antimicrobial drug concentrate, that can be orally administered to an animal in combination with its drinking water, comprising:

(a) a sulfonamide and/or sulfonamide salt in aqueous solution;

(b) a micronized 2,4-diaminopyrimidine in stable suspension within said solution; and (c) xanthan gum.

* * * * *